United States Patent [19]

Ondetti

[11] 4,192,945
[45] Mar. 11, 1980

[54] PROCESS FOR PREPARING PROLINE AND HOMOPROLINE DERIVATIVES

[75] Inventor: Miguel A. Ondetti, Princeton, N.J.

[73] Assignee: E. R. Squibb & Sons, Inc., Princeton, N.J.

[21] Appl. No.: 20,580

[22] Filed: Mar. 15, 1979

Related U.S. Application Data

[62] Division of Ser. No. 967,335, Dec. 7, 1978.

[51] Int. Cl.$^2$ .................. C07D 207/16; C07D 211/60
[52] U.S. Cl. ............................. 546/245; 260/239.3 B; 260/326.2; 424/267; 424/274
[58] Field of Search ...................... 546/245; 260/326.2

[56] References Cited

U.S. PATENT DOCUMENTS 4,105,776  8/1978  Ondetti et al. ........................ 424/274

*Primary Examiner*—Alan L. Rotman
*Assistant Examiner*—Robert T. Bond
*Attorney, Agent, or Firm*—Lawrence S. Levinson; Donald J. Barrack

[57] ABSTRACT

Compounds having the formula

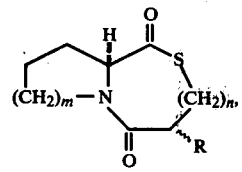

wherein R is hydrogen or alkyl, n is 0 or 1 and m is 1 or 2 have hypotensive activity. Those compounds of the above formula wherein n is 1 are useful intermediates for the preparation of other hypotensive agents having the formula

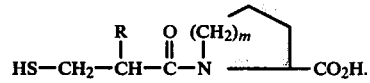

6 Claims, No Drawings

PROCESS FOR PREPARING PROLINE AND HOMOPROLINE DERIVATIVES

This is a division, of application Ser. No. 967,335, filed Dec. 7, 1978.

BACKGROUND OF THE INVENTION

U.S. Pat. No. 4,105,776, issued Aug. 8, 1978 described a group of thioalkanoyl derivatives of azetidine, pyrrolidine- and piperidinecarboxylic acid derivatives which are useful as inhibitors of the conversion of the decapeptide angiotensin I to angiotensin II, and are therefore useful in reducing or relieving angiotensin related hypertension.

Among the compounds described in the abovementioned patent are those having the structural formula

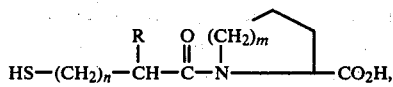

wherein the variables are as defined hereinafter.

BRIEF DESCRIPTION OF THE INVENTION

Compounds having the formula

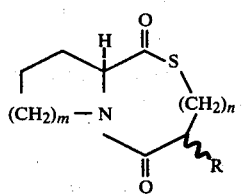

I have hypotensive activity. In formula I, and throughout the specification, the symbols are as defined below:

R is hydrogen or alkyl of 1 to 7 carbon atoms (methyl is the preferred alkyl group);

m is 1 or 2; and n is 0 or 1.

Those compounds of formula I wherein n is 1 are also useful as intermediates in a novel process for the preparation of compounds having the formula

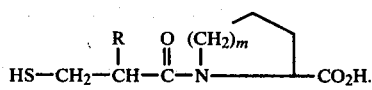

II

DETAILED DESCRIPTION OF THE INVENTION

The compounds of formula I are useful as hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one or a combination of compounds of formula I, angiotensin dependent hypertension in the species of mammal suffering therefrom is alleviated. A single dose, or preferably two to four divided daily doses, provided on a basis of about 0.1 to 100 mg. per kilogram per day, preferably about 1 to 50 mg. per kilogram per day is appropriate to reduce blood pressure. The substance is preferably administered orally, but parenteral routes such as the subcutaneous, intramuscular, intravenous or intraperitoneal routes can also be employed.

The compounds of formula I can be formulated for use in the reduction of blood pressure in compositions such as tablets, capsules or elixirs for oral administration or in sterile solutions or suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The products of formula I can be prepared by cyclization of the corresponding compound having the formula

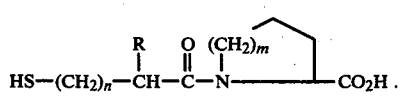

III

The cyclization can be accomplished using procedures known in the art for the cyclization of peptides; see Bodanszky et al., Peptide Synthesis, John Wiley & Sons, 1976,p.190. The cyclization reaction can be run using a coupling reagent, e.g., a carbodiimide, N,N'-carbonylbisimidazole, 1-ethoxycarbonyl-2-ethoxy-1,2-dihydroquinoline or a diphenylphosphorazidate. An exemplary procedure comprises treating a compound of formula III with 1-cyclohexyl-3-(2-morpholinoethyl) carbodiimide metho-p-toluenesulfonate in an organic solvent, e.g., a halogenated hydrocarbon such as dichloromethane, in an inert atmosphere, e.g., argon or nitrogen.

In addition to being useful as hypotensive agents, those compounds of formula I wherein n is 1 are useful as intermediates in a process for preparing compounds of formula II. Hydrolysis of a compound of formula I (n is 1), e.g., with alkali, yields the corresponding product of formula II. The hydrolysis reaction can be run in an organic solvent, e.g., dimethylformamide, preferably in an inert atmosphere, e.g., argon or nitrogen. The reaction can conveniently be run at room temperature.

When the compounds of formula I (n is 1) are to be used as intermediates for the preparation of the corresponding product of formula II they will of course not be prepared using the previously described synthesis. An alternate synthesis comprises as a first step the addition of a suitably protected carbothioic acid having the formula

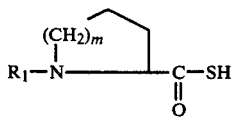

to an acrylic acid having the formula

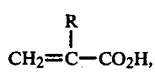

to obtain a compound having the formula

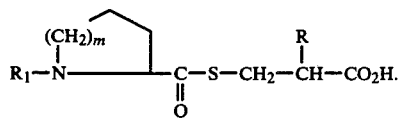

In formulas IV and VI, and throughout the specification, the symbol $R_1$ is a suitable amino protecting group, e.g., an alkoxycarbonyl such as t-butyloxycarbonyl or t-amyloxycarbonyl, an aryloxycarbonyl such as benzyloxycarbonyl, etc. The reaction can be run in an organic solvent, e.g., a halogenated hydrocarbon such as chloroform, preferably in a inert atmosphere such as argon or nitrogen. The reaction proceeds most readily at the reflux temperature of the solvent.

The carbothioic acids of formula IV are prepared using art-recognized procedures. For example, a mixed anhydride of a protected amino acid having the formula

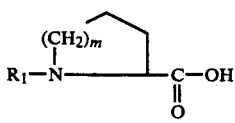

can be treated with sodium hydrosulfide to yield the corresponding carbothioic acid.

The compounds of formula VI can also be obtained by reacting an activated derivative of a protected amino acid of formula VII with a salt of a mercapto acid having the formula

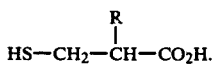

Exemplary of the activated derivatives contemplated are mixed anhydrides and the imidazolide derivative obtained by reacting a compound of formula VII with N,N'-carbonylbisimidazole.

Cleavage of the protecting group from a compound of formula VI can also be accomplished using art-recognized procedures. For example, treatment of a compound of formula VI with a mixture of trifluoroacetic acid and anisole will remove the protecting group ($R_1$). Cyclization of the resulting compound using one of the procedures described above for cyclization of a compound of formula III yields the corresponding compound of formula I (n is 1).

The compounds formula I contain two asymmetrical carbon atoms and exist as mixtures of diastereoisomers. The S (or L) configuration is preferred for the carbon alpha to the nitrogen atom.

The following examples are specific embodiments of this invention.

EXAMPLE 1

(4S,9aS)-Hexahydro-4-methyl-1H,5H-pyrrolo-[2,1-c][1,4]-thiazepine-1,5-dione.

1-[D-3-Mercapto-2-methylpropanoyl]-L-proline (S,S) (5.425 g) is taken into 200 ml of dichloromethane and added dropwise to a stirred solution of 1-cyclohexyl-3-(2-morpholineoethyl) carbodiimide metho-p-toluene-sulfonate (50 g) in 2.2 liters of dichloromethane under argon. The reaction is stored for three days at room temperature. The dichloromethane is removed in vacuo. The residue is taken into ethyl acetate, washed with 10% potassium sulfate, water, saturated sodium bicarbonate, water, dried over magnesium sulfate, and concentrated to dryness in vacuo. This material (1.7 g) is crystallized from ethyl acetate-hexane to yield 1.4 g of the title compound, melting point 103°–104° C.

EXAMPLE 2

1-(3-Mercapto-2-methylpropanoyl)-L-proline (RS,S)

(A)

1-(tert-Butyloxycarbonyl)-L-2-pyrrolidinecarbothioic acid.

A solution of 1-(tert-butyloxycarbonyl)-L-proline (8.6 g) and triethylamine (5.56 ml) in dry tetrahydrofuran (300 ml) is cooled to −15° C. under argon and treated with ethyl chloroformate (3.84 ml). After stirring at −15° C. for 90 minutes, sodium hydrosulfide (4.0 g) is added, and the stirring is continued for about 16 hours. The mixture is acidified with aqueous hydrochloric acid, extracted with ether, and the extracts are washed with brine, dried and evaporated to dryness to yield the title compound.

(B)

3-[1-(tert-Butyloxycarbonyl)-L-prolylthio]-2-methylpropanoic acid.

Method I

A mixture of 1-(tert-butyloxycarbonyl)-L-2-pyrrolidine carbothioic acid (2.3 g), methacrylic acid (0.86 g) and chloroform (5 ml) is refluxed under argon until all the methacrylic acid has reacted (nmr spectroscopy). The mixture is concentrated to dryness and chromatographed on a silica gel column with benzene-acetic acid to yield the title compound.

Method II

To a chilled solution of 1-t-butoxycarbonyl-L-proline (2.15 g) in dichloromethane (20 ml) is added N,N'-carbonylbisimidazole (1.62 g) and the mixture is stirred in an ice bath for 1 hour. A solution of 3-methyl-2-methylpropionic acid (1.2 g) and triethylamine (1.4 ml) in dichloromethane (5 ml) is added and the mixture is stirred at room temperature for about 16 hours. The solvent is removed in vacuo, the residue dissolved in ethyl acetate, washed with 10% aqueous potassium bisulfate and water, dried and concentrated to give the title compound.

(C)
(4RS-9aS)-Hexahydro-4-methyl-1H,5H-pyrrolo-[2,1-c][1,4]thiazepine-1,5-dione.

3-[1-(tert-butyloxycarbonyl)-L-prolylthio]-2-methylpropanoic acid (2.3 g) is dissolved in a mixture of trifluoroacetic acid (15 ml) and anisole (1.1 g). After fifteen minutes at room temperature the mixture is concentrated to dryness in vacuo and the residue triturated with ether-hexane (1:1). The insoluble material is dried in vacuo, dissolved in dichloromethane (100 ml) and added dropwise to a stirred solution of 1-cyclohexyl-3-(2-morpholino-ethyl) carbodiimide metho-p-toluene sulfonate (20 g) in 900 ml of dichloromethane under argon. The reaction mixture is stored at room temperature for three days and the dichloromethane is then removed in vacuo. The residue is dissolved in ethyl acetate and the solution is washed with 10% potassium biculfate, water, saturated sodium bicarbonate and water. The organic layer is dried and concentrated to give the title compound.

(D) 1-(3-Mercapto-2-methylpropanoyl)-L-proline (RS,S).

To a solution of (4RS-9aS)-hexahydro-4-methyl-1H,5H-pyrrolo[2,1-c][1,4]thiazepine-1,5-dione (2 g) in dimethylformamide (100 ml), normal sodium hydroxide (20 ml) is added. The mixture is stirred for four hours at room temperature under argon. The solvent is removed in vacuo, the residue is dissolved in ethyl acetate and washed with 10% potassium bisulfate and water. The organic layer is dried and concentrated to yield the title compound.

EXAMPLE 3

(4RS, 10aS)-Hexahydro-4-methyl-5H-pyrido [2,1-c][1,4]thiazepine-1,5(7H)-dione

Following the procedure of Example 2, but substituting 1-(t-butyloxycarbonyl)-L-pipecolic acid for 1-(t-butyloxycarbonyl)-L-proline, yields the title compound. Either of the methods described in Example 2B can be used.

EXAMPLE 4

(3RS,8aS)-Tetrahydro-3-methyl-1H-pyrrolo [2,1-c][1,4]thiazine-1,4(3H)-dione

Following the procedure of Example 2 (using Method II in part B), but substituting 2-mercaptopropionic acid for 3-mercapto-2-methylpropionic acid, yields the title compound.

What is claimed is:

1. A process for preparing a compound having the formula

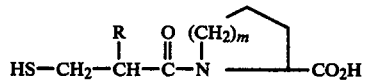

which comprises hydrolyzing the corresponding compound having the formula

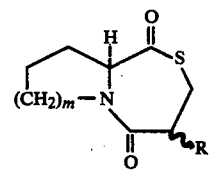

wherein R is hydrogen or alkyl of 1 to 7 carbon atoms and m is 1 or 2.

2. A process in accordance with claim 1 wherein m is 1.

3. A process in accordance with claim 1 wherein m is 2.

4. A process in accordance with claim 1 wherein R is hydrogen.

5. A process in accordance with claim 1 wherein R is alkyl of 1 to 7 carbon atoms.

6. A process in accordance with claim 5 wherein R is methyl.

* * * * *